United States Patent
De Faveri et al.

(10) Patent No.: US 11,332,478 B2
(45) Date of Patent: May 17, 2022

(54) MANUFACTURE OF 4,5,6,7-TETRAHYDROISOXAZOLO[5,4-C]PYRIDIN-3-OL

(71) Applicant: H. Lundbeck A/S, Valby (DK)

(72) Inventors: Carla De Faveri, Farra di Soligo TV (IT); Florian Anton Martin Huber, Dolo VE (IT)

(73) Assignee: H. Lundbeck A/S, Valby (DK)

( * ) Notice: Subject to any disclaimer, the term of this patent is extended or adjusted under 35 U.S.C. 154(b) by 176 days.

(21) Appl. No.: 16/828,141

(22) Filed: Mar. 24, 2020

(65) Prior Publication Data

US 2020/0223865 A1 Jul. 16, 2020

Related U.S. Application Data

(62) Division of application No. 15/559,630, filed as application No. PCT/EP2016/056244 on Mar. 22, 2016, now Pat. No. 10,626,123.

(30) Foreign Application Priority Data

Mar. 24, 2015 (DK) .............................. PA201500181

(51) Int. Cl.
| | | |
|---|---|---|
| *C07D 498/04* | (2006.01) | |
| *C07D 491/113* | (2006.01) | |
| *C07D 211/78* | (2006.01) | |
| *C07C 269/04* | (2006.01) | |
| *C07C 227/22* | (2006.01) | |
| *C07C 227/18* | (2006.01) | |
| *C07C 249/02* | (2006.01) | |
| *C07C 271/22* | (2006.01) | |
| *C07C 229/08* | (2006.01) | |

(52) U.S. Cl.
CPC .......... *C07D 498/04* (2013.01); *C07C 227/18* (2013.01); *C07C 227/22* (2013.01); *C07C 229/08* (2013.01); *C07C 249/02* (2013.01); *C07C 269/04* (2013.01); *C07C 271/22* (2013.01); *C07D 211/78* (2013.01); *C07D 491/113* (2013.01)

(58) Field of Classification Search
CPC .............. C07D 498/04; C07D 491/113; C07D 211/78; C07C 269/04; C07C 227/22; C07C 227/18; C07C 249/02
USPC ........................... 548/242; 546/301, 341, 113
See application file for complete search history.

(56) References Cited

U.S. PATENT DOCUMENTS

| | | |
|---|---|---|
| 4,923,880 A | 5/1990 | Krogsgaard-Larsen et al. |
| 7,371,863 B2 | 5/2008 | Petersen et al. |
| 10,626,123 B2 | 4/2020 | De Faveri et al. |

FOREIGN PATENT DOCUMENTS

| | | |
|---|---|---|
| EP | 0000338 B1 | 11/1981 |
| JP | S54-036290 A | 3/1979 |
| JP | 2007-504179 A | 3/2007 |
| WO | WO 1997/002813 A | 1/1997 |
| WO | WO 2004/112786 A2 | 12/2004 |
| WO | WO 2005/023820 A1 | 3/2005 |
| WO | WO 2008/124703 A2 | 10/2008 |
| WO | WO 2016/150953 A1 | 9/2016 |

OTHER PUBLICATIONS

U.S. Appl. No. 15/559,630, filed Sep. 19, 2017, De Faveri et al.
PCT/EP2018/056244, dated Aug. 12, 2016, International Search Report and Written Opinion.
International Search Report and Written Opinion for PCT/EP2016/056244 dated Aug. 12, 2016.
[No Author Listed], CAS Registry No. 85118-32-7. Database Registry Online; Chemical Abstracts Service, Columbus, Ohio, US. XP002308640. 2004. 1 page.
Costa et al., Benzodiazepines on trial: a research strategy for their rehabilitation. Trends Pharmacol Sci. May 1996;17(5):192-200. doi: 10.1016/0165-6147(96)10015-8.
Gaba et al., GABA-uptake inhibitors: construction of a general pharmacophore model and successful prediction of a new representative. J Med Chem. Aug. 1991;34(8):2547-57. doi: 10.1021/jm00112a032.
Garst et al., Specific Enolates from a-Amino Ketones. J Organ Chem. 1980;45(12):2307-2315.
Knight et al., β-Hydroxypiperidinecarboxylates: additions to the chiral pool from bakers' yeast reductions of β-ketopiperidinecarboxylates. J Chem Soc, Perkin Trans 1. 1998;22:3673-3684. doi: 10.1039/A807313I.
Krogsgaard-Larsen et al., Muscimol Analogues. II. Synthesis of Some Bicyclic 3-Isoxazolo Zwitterions. Acta Chem Scand B. 1977:31584-588.
Rong et al., Synthesis of 4,5,6,7-tetrahydroisoxazolo[5,4-c]pyridin-3(2H)-one(gaboxadol). Chin J Med Chem. 2007;17(3):166-169.
Sauerberg et al.,. A novel class of conformationally restricted heterocyclic muscarinic agonists. J Med Chem. Jun. 1986;29(6):1004-9. doi: 10.1021/jm00156a018.
Yuan et al., [Synthesis of 4-[(4-chlorophenyl) (5-fluoro-2-hydroxyphenyl) methylene amino]butyrates and its anticonvulsant activity]. Hua Xi Yi Ke Da Xue Xue Bao. Sep. 1990;21(3):310-4. Article in Chinese.

*Primary Examiner* — Joseph R Kosack
*Assistant Examiner* — Sagar Patel
(74) *Attorney, Agent, or Firm* — Wolf, Greenfield & Sacks, P.C.

(57) ABSTRACT

The present invention relates to a process for synthesis of 4,5,6,7-tetrahydroisoxazolo[5,4-c]pyridin-3-ol abbreviated THIP, having the INN name gaboxadol, starting from pyrrolidin-2-one. The process comprises a new direct process to obtain the intermediate dimethyl 5-hydroxy-3,6-dihydropyridine-1,4(2H)-dicarboxylate or the intermediate diethyl 5-hydroxy-3,6-dihydropyridine-1,4(2H)-dicarboxylate.

13 Claims, No Drawings

MANUFACTURE OF 4,5,6,7-TETRAHYDROISOXAZOLO[5,4-C] PYRIDIN-3-OL

CROSS REFERENCE TO RELATED APPLICATIONS

This application is a divisional of U.S. application Ser. No. 15/559,630, (filed Sep. 19, 2017); which is a § 371 national stage entry of PCT/EP2016/056244 (filed on Mar. 22, 2016); which application claims priority to Danish Patent Application PA 2015 00181 (filed on Mar. 24, 2015), each of which applications is incorporated herein by reference in their entirety.

FIELD OF THE INVENTION

The present invention relates to a process for synthesis of 4,5,6,7-tetrahydroisoxazolo[5,4-c]pyridin-3-ol abbreviated THIP, having the INN name gaboxadol, starting from pyrrolidin-2-one. The process comprises a new direct process to obtain the intermediate dimethyl 5-hydroxy-3,6-dihydropyridine-1,4(2H)-dicarboxylate or the intermediate diethyl 5-hydroxy-3,6-dihydropyridine-1,4(2H)-dicarboxylate.

BACKGROUND

The compound 4,5,6,7-tetrahydroisoxazolo[5,4-c]pyridin-3-ol abbreviated THIP, having the INN name gaboxadol, was disclosed for the first time in EP Patent No. 0000338 and has the molecular structure depicted below.

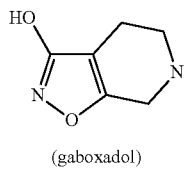

(gaboxadol)

Gaboxadol is a GABAA receptor agonist with functional selectivity for the delta containing GABAA receptor. Gaboxadol has been suggested for use in treating a variety of neurological and psychiatric disorders such as epilepsy, Parkinson's disease, schizophrenia and Huntington's chorea. WO 97/02813 discloses the use of gaboxadol for treatment of sleep disorders, and positive results have been obtained in pre-clinical models of depression (WO 2004/112786).

Gaboxadol may be prepared using methods that are well known in the art. EP 0000338 and Krogsgaard-Larsen, Acta Chem. Scand. B, (1977), 31: 584-588 disclose a process wherein gaboxadol is prepared from ethyl-1-benzyl-3-oxopiperidine-4-carboxylate. Rong and Chang, Chin. J. Med. Chem. (2007), 17:166-169 disclose a process for manufacture of gaboxadol starting from glycine ester hydrochloride, benzyl chloride and γ-butyrolactone. WO 2005/023820 discloses a process for manufacture of gaboxadol from 3,N-Dihydroxy-isonicotinamide as starting material via the intermediate isoxazolo[5,4-c]pyridin-3-ol (HIP).

There is a need for a superior alternative to the current manufacturing processes of gaboxadol with respect to parameters such as cost-effectiveness, safety, robustness and applicability for industrial scale.

SUMMARY OF THE INVENTION

The present inventors have found a new process for synthesis of gaboxadol comprising a direct process to obtain dimethyl 5-hydroxy-3,6-dihydropyridine-1,4(2H)-dicarboxylate, a key intermediate in the gaboxadol synthesis. The process has the advantages of being a cost-effective industrial process with a good atom-economy (avoiding the use of a bulky protection group) starting from cheap and readily available starting materials. A further advantage of the process is that it is suitable for industrial upscaling.

In one embodiment, the invention relates to a process for the manufacture of gaboxadol, or for the manufacture of the compound of formula VI below,

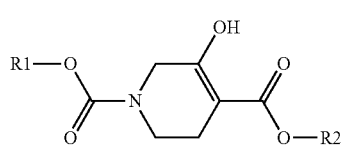

VI wherein both of R1 and R2 are either methyl or ethyl, said process comprising the following step, a) reacting a compound of formula I,

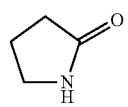

I with an anhydrous acid and a methyl alcohol or ethyl alcohol to obtain a compound of formula II,

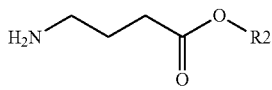

II wherein R2 is methyl when methyl alcohol is applied in the reaction, and ethyl when ethyl alcohol is applied in the reaction.

In another embodiment, the invention relates to a process for the manufacture of gaboxadol, or for the manufacture of the compound of formula VI below,

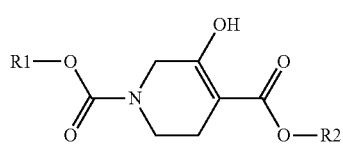

VI wherein both of R1 and R2 are either methyl or ethyl, said process comprising the following steps, b) reacting the compound of formula II

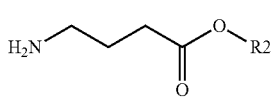

II with a base and methyl- or ethyl glyoxylate to obtain a compound of formula III,

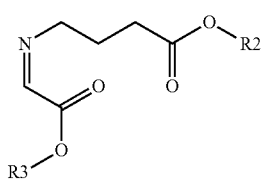

c) converting the compound of formula III to a compound of formula IV by hydrogenation

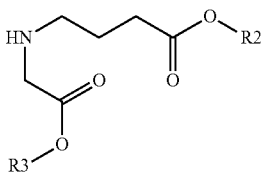

d) reacting the compound of formula IV with methyl- or ethyl chloroformate to obtain the compound of formula V

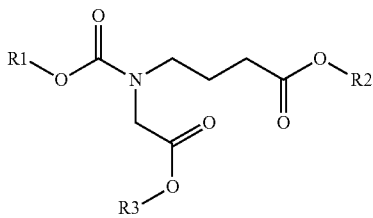

wherein R1 is methyl when methyl chloroformate is applied in the reaction, or ethyl
when ethyl chloroformate is applied in the reaction, and
wherein R2 independently represents methyl or ethyl, and
wherein R3 is methyl when methyl glyoxylate is applied in the reaction, or ethyl when ethyl glyoxylate is applied in the reaction.

In another embodiment, the invention relates to a process for the manufacture of gaboxadol, or for the manufacture of the compound of formula VI below,

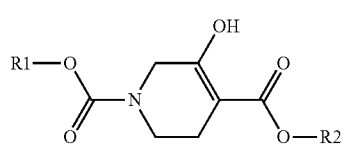

said process comprising the following step,
e) reacting the compound of formula V

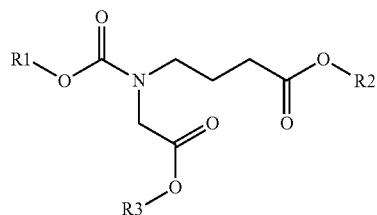

with sodium methoxide in methanol or sodium ethoxide in ethanol to obtain the compound of formula VI,

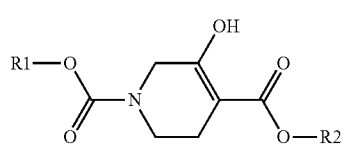

wherein R1, R2 and R3 of the compound of formula V independently represents methyl or ethyl, and wherein R1 and R2 of the compound of formula VI are both methyl when sodium methoxide in methanol is applied in the reaction, or R1 and R2 of the compound of formula VI are both ethyl when sodium ethoxide in ethanol is applied in the reaction.

In one embodiment, the invention relates to a process for the manufacture of gaboxadol, or for the manufacture of the compound of formula VI, said process comprising all the process steps a), b), c), d) and e) presented above.

Definitions

Throughout the description, the term "gaboxadol" is intended to include any form of the compound, such as the free base (zwitter ion) and pharmaceutically acceptable salts. The zwitterion and pharmaceutically acceptable salts include anhydrates and solvates such as hydrates. Free base and salts and anhydrates and solvates thereof, include amorphous and crystalline forms. In a particular embodiment, gaboxadol is in the form of a monohydrate. In another particular embodiment, gaboxadol or pharmaceutically acceptable salts thereof is crystalline, such as the crystalline hydrochloric acid salt, the crystalline hydrobromic acid salt, or the crystalline zwitter ion monohydrate.

DETAILED DESCRIPTION OF THE INVENTION

The objective of the present invention is to find a robust, safe and cost-effective process for synthesis of gaboxadol.

The present inventors have found a direct process to obtain the carbamate intermediate (Compound VI in scheme 1 below), which is a key intermediate in the gaboxadol synthesis. The process starts from Pyrrolidin-2-one which is a cheap and readily available starting material. Compared to processes disclosed in prior art, the process of the present invention has the advantage of having good atom-economy since the intermediate dimethyl 5-hydroxy-3,6-dihydropyridine-1,4(2H)-dicarboxylate is obtained directly with no need of using an N-benzyl protecting group.

In brief, the synthesis is described in Scheme 1 below.

said anhydrous acid is methanesulfonic acid. In a further embodiment, the ring opening is performed in a one pot synthesis providing the methanesulfonic acid salt of Compound II, depicted as compound IIb below.

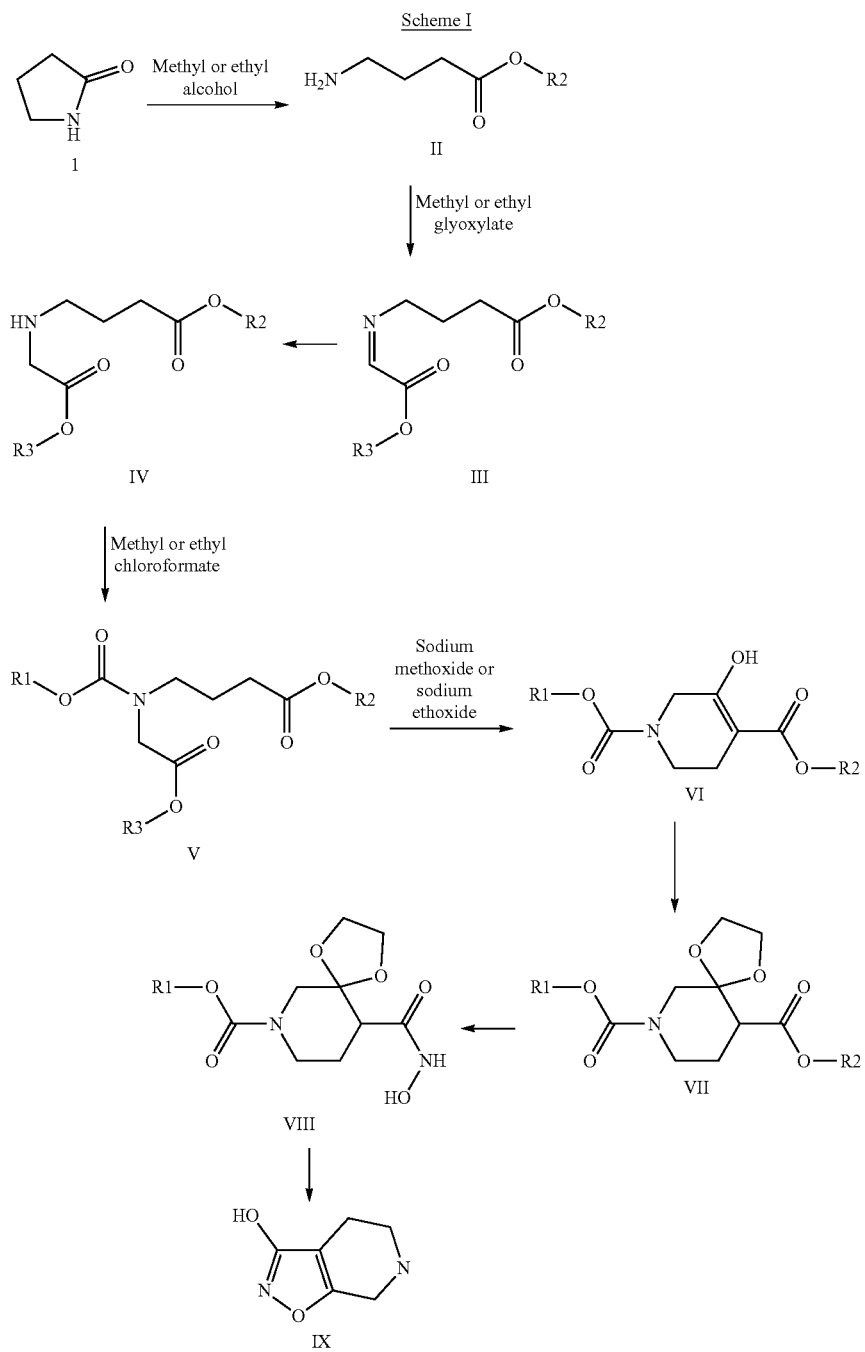

R1, R2 and R3 independently represent methyl or ethyl.

The first step comprises a simultaneous ring opening and esterification of pyrrolidin-2-one (Compound I) with methyl- or ethyl alcohol, using an anhydrous acid to afford the compound of formula II, which is isolated as a solid. By using an anhydrous acid in the ring-opening of Compound I, this part of the process takes place in water free conditions which gives Compound II in good yield. In one embodiment

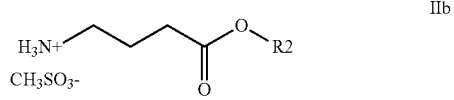

The subsequent steps (Compounds II to V) are sequential without isolation of the intermediates. First, the Compound II is reacted with methyl glyoxylate or ethyl glyoxylate in a non-polar solvent in the presence of a base, to form the imine (Compound III). In one embodiment, said base is potassium carbonate. In a preferred embodiment, said base is triethylamine. In one embodiment, said non-polar solvent is heptane. In a preferred embodiment, said non-polar solvent is toluene. In one embodiment, the reaction is performed with triethylamine, and a ionic liquid solution is formed in situ in the form of triethylammonium methanesulfonate. The triethylammonium methanesulfonate takes up all the water and the reaction can proceed without the need of additional dehydrating agents. Furthermore, the ionic liquid and water forms a separate layer, which at the end of reaction can be separated from the product containing layer.

Compound III is transformed into Compound IV by catalytic hydrogenation e.g. by using palladium on charcoal.

Compound IV is reacted with methyl- or ethyl chloroformate to form Compound V as an intermediate of the process. Compound V can be purified by washing with acidified water, by distillation or by a combination of these two purification strategies. In one embodiment, Compound V is purified by thin-film distillation to obtain Compound V as a colourless oil.

Compound V is converted to compound VI by a ring-closure (Dieckmann condensation) by addition of sodium methoxide or sodium ethoxide, to give Compound VI. The conditions applied in the Dieckmann condensation afford compound VI in high yield and avoid formation of excessive amounts of the undesired compound depicted below.

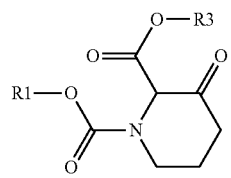

Compound VI can be present either as enol or as its keto form (keto-enol tautomerism). As a ketone it can react with methylene- or ethylene glycol, preferably ethylene glycol to form a ketal protecting group, providing compound VII.

Subsequently Compound VII is transformed into the hydroxamic acid (Compound VIII) with hydroxylamine. Compound VIII is isolated as a solid.

Synthesis of gaboxadol (Compound IX) from Compound VIII has been described in EP 0000338 and in Krogsgaard-Larsen, Acta Chem. Scand. B, 1977, 31: 584-588.

Embodiments According to the Invention

In the following, embodiments of the invention are disclosed. The first embodiment is denoted E1, the second embodiment is denoted E2 and so forth.

E1. A process for the manufacture of the compound of formula VI below,

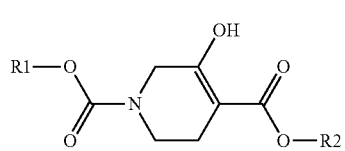

wherein both of R1 and R2 are either methyl or ethyl, said process comprising the following step, a) reacting a compound of formula I,

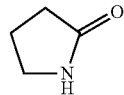

with an anhydrous acid and a methyl alcohol or ethyl alcohol to obtain a compound of formula II,

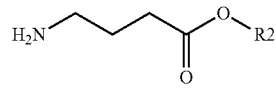

wherein R2 is methyl when methyl alcohol is applied in the reaction, and ethyl when ethyl alcohol is applied in the reaction.

E2. The process according to embodiment 1, wherein said anhydrous acid is anhydrous methanesulfonic acid.

E3. The process according to embodiment 2, wherein the compound of formula II is obtained as a methane sulfonic acid salt depicted as formula IIb

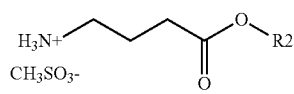

wherein R2 is methyl when methyl alcohol is applied in the reaction, and ethyl when ethyl alcohol is applied in the reaction.

E4. The process according to embodiment 3, wherein the compound of formula IIb is obtained by a one-pot synthesis.

E5. The process according to any of embodiments 1-4, said process comprising the further steps, b) reacting the compound of formula II or IIb

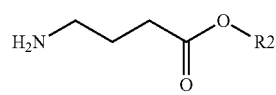

with a base and methyl- or ethyl glyoxylate to obtain a compound of formula III,

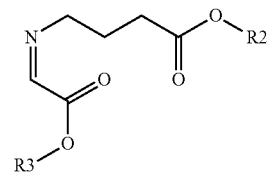

c) converting the compound of formula III to a compound of formula IV by hydrogenation

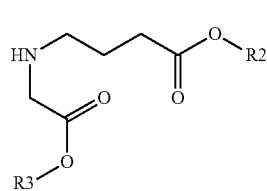

IV d) reacting the compound of formula IV with methyl- or ethyl chloroformate to obtain the compound of formula V

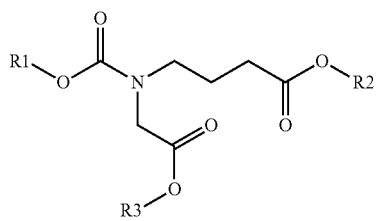

V wherein R1 is methyl when methyl chloroformate is applied in the reaction, or ethyl when ethyl chloroformate is applied in the reaction, and wherein R2 is methyl when methyl alcohol is applied in the reaction, or ethyl when ethyl alcohol is applied in the reaction, and wherein R3 is methyl when methyl glyoxylate is applied in the reaction, or ethyl when ethyl glyoxylate is applied in the reaction.

E6. The processes according to embodiment 5, wherein the steps a), b), c) and d) are carried out in toluene.

E7. A process for the manufacture of the compound of formula VI below,

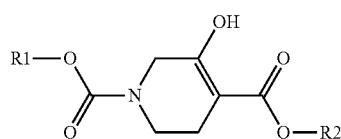

VI wherein both of R1 and R2 are either methyl or ethyl, said process comprising the following steps, b) reacting a compound of formula II or IIb

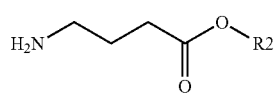

II with a base and methyl- or ethyl glyoxylate to obtain a compound of formula III,

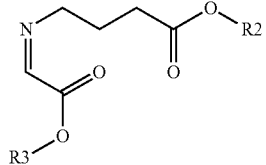

III c) converting the compound of formula III to a compound of formula IV by hydrogenation

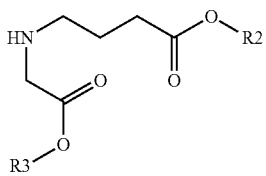

IV d) reacting the compound of formula IV with methyl- or ethyl chloroformate to obtain the compound of formula V

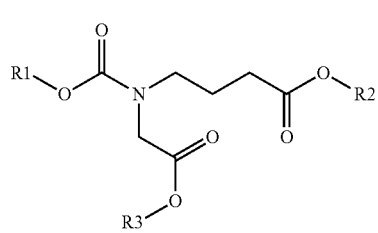

V wherein R1 is methyl when methyl chloroformate is applied in the reaction, or ethyl when ethyl chloroformate is applied in the reaction, and wherein R2 independently represents methyl or ethyl, and wherein R3 is methyl when methyl glyoxylate is applied in the reaction, or ethyl when ethyl glyoxylate is applied in the reaction.

E8. The processes according to embodiment 7, wherein the steps b), c) and d) are carried out in toluene.

E9. The process according to any of embodiments 5-8, wherein the base used in step b) is triethylamine.

E10. The process according to any of embodiments 5-9, wherein the compound of formula V is purified by washing with acidified water or by distillation or by a combination of these two purification strategies E11. The process according to any of embodiments 5-10, wherein the compound of formula V is purified by thin-film distillation.

E12. The process according to any of embodiments 1-11, said process comprising the further step e) reacting the compound of formula V

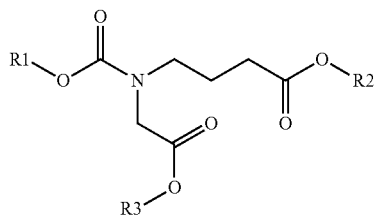

with sodium methoxide in methanol or sodium ethoxide in ethanol to obtain the compound of formula VI,

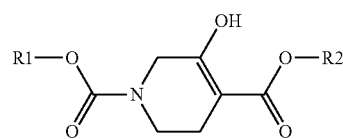

wherein R1, R2 and R3 of the compound of formula V independently represents methyl or ethyl, and R1 and R2 of the compound of formula VI are both methyl when sodium methoxide in methanol is applied in the reaction, or R1 and R2 of the compound of formula V1 are both ethyl when sodium ethoxide in ethanol is applied in the reaction, E13. A process for the manufacture of the compound of formula VI below,

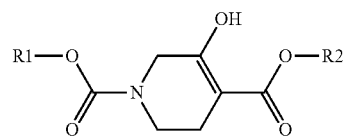

said process comprising the following step, e) reacting a compound of formula V

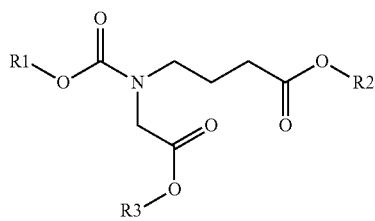

with sodium methoxide in methanol or sodium ethoxide in ethanol to obtain the compound of formula VI,

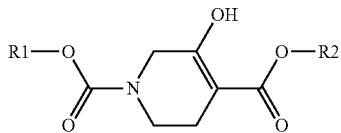

wherein R1, R2 and R3 of the compound of formula V independently represents methyl or ethyl, and wherein R1 and R2 of the compound of formula VI are both methyl when sodium methoxide in methanol is applied in the reaction, or R1 and R2 of the compound of formula VI are both ethyl when sodium ethoxide in ethanol is applied in the reaction.

E14. The process according to any of embodiments 12-13, wherein step e) is carried out in toluene, preferably 2-6 volumes of toluene such as 3-5 volumes of toluene such as about 4 volumes of toluene.

E15. The process according to any of embodiments 12-14, wherein the reaction in step e) is carried out at a temperature between 70 and 85° C.

E16. The process according to any of embodiments 12-15, wherein the reaction in step e) is carried out at reflux temperature.

E17. A process for the manufacture of the compound of formula VI, said process comprising all the steps a), b), c), d) and e) according to any of embodiments 1-16.

E18. The process according to any of embodiments 1-17, wherein the compound of formula VI is subsequently converted to the compound of formula IX,

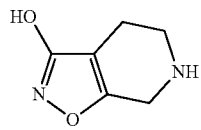

which is gaboxadol.

E19. A process for the manufacture of gaboxadol, wherein compound VI is an intermediate of said process, and wherein said compound VI is manufactured by a process according to any of embodiments 1-17.

E20. A process for the manufacture of gaboxadol, said process comprising manufacturing a compound of formula VI by the process according to any of embodiments 1-17, and subsequently manufacturing gaboxadol starting from said compound of formula VI.

E21. The process according to any of embodiments 18-20, said process comprising a step wherein the compound of formula VI is reacted with ethylene glycol to obtain the compound of formula VII,

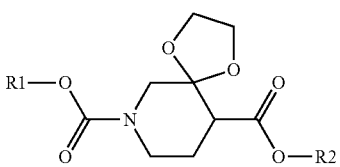

wherein both of R1 and R2 are either methyl or ethyl.

E22. The process according any of embodiments 18-21, said process comprising a step wherein the compound of formula VII is reacted with hydroxylamine to obtain the compound of formula VIII

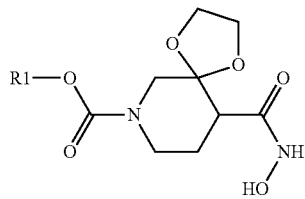

VIII wherein R1 represents methyl or ethyl.

E23. The process according to any of embodiments 18-22, said process comprising a step wherein the compound of formula VIII is converted to the compound of formula IX,

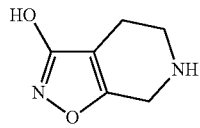

IX which is gaboxadol.

E24. The compound of formula VI below,

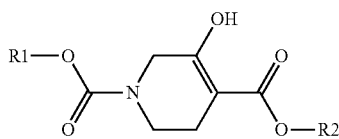

VI wherein both of R1 and R2 are either methyl or ethyl, obtained by a process according to any of embodiments 1-17.

E25. The compound of formula IX,

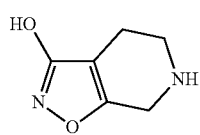

IX which is gaboxadol, obtained by the process according to any of embodiments 1-23.

E26. A compound of formula V,

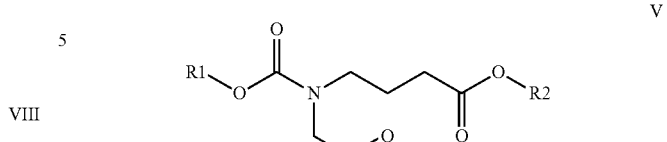

V wherein all of R1, R2 and R3 are methyl.

E27. A compound of formula IIb,

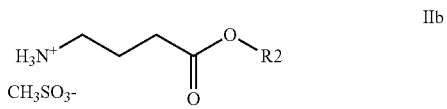

IIb wherein R2 is methyl or ethyl.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a process described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

The invention will be illustrated by the following non-limiting examples.

EXAMPLES

Example 1

Synthesis of ethyl 4-aminobutyrate, Methanesulfonic Acid Salt (Compound IIb)

A reactor was charged at room temperature with pyrrolidin-2-one (400 kg), toluene (1044 kg) and ethanol (316 kg). Anhydrous methanesulfonic acid (492 Kg) was added to the solution. The mixture was heated up to T=110-115° C., P=1.5-2 bar and kept under stirring for 22 hours. The mixture was then cooled down to T=60-65° C. and then it was diluted with toluene (696 kg). The suspension was cooled down to T=50-55° C. and kept under stirring for one hour and then further cooled down to T=20-30° C. in 1.5 hours. The suspension was maintained under stirring for 1 hour then the solid was isolated by centrifuge and washed with toluene. The wet solid was dried under vacuum at T=45-50° C. for two hours and then at T=50-55° C. for 15 hours yielding to 1062 Kg of ethyl 4-aminobutyrate, methanesulfonic acid salt.

Example 2

The procedure described in example 1 was repeated yielding 1059 kg of ethyl 4-aminobutyrate, methanesulfonic acid salt.

Example 3

Synthesis of ethyl 4-((2-ethoxy-2-oxoethyl (methoxycarbonyl)amino)butanoate (Compound V)

A reactor was charged at room temperature under nitrogen with ethyl 4-aminobutyrate methanesulfonic acid salt (616 kg), toluene (2088 kg) and ethyl glyoxylate 50% in toluene (500 kg). The suspension was cooled down to T=−2° C. Triethylamine (275 kg) was added in 90 minutes keeping the temperature in the range −2-2° C. The mixture was stirred for 2.5 hours and then diluted with toluene (522 kg). The upper layer containing ethyl (E)-4-((2-ethoxy-2-oxoethylidene)amino)butanoate was separated at T=0° C. and transferred into an autoclave. The solution was hydrogenated at T=10-15° C. and hydrogen pressure of 1.0-1.5 bar in the presence of anhydrous sodium sulfate (100 kg) and Pd/C 10% (18 kg as wet catalyst). When the hydrogen uptake was finished the mixture was heated up to T=15-20° C. and diluted with water (700 L) keeping the temperature in the range T=20-25° C. The catalyst was removed by filtration. The filter was washed with toluene (348 kg). The whole solution was transferred into another reactor containing potassium carbonate (360 kg). The mixture was cooled down to T=−5-0° C. Methyl chloroformate (226 kg) was added in eight hours maintaining the temperature in the range T=−5-2° C. The mixture was then treated with water (600 L) at T=0-5° C. and stirred for about two hours and then was heated to 40-45° C. The aqueous layer was separated and washed at T=40-45° C. with water (1200 L), diluted hydrochloric acid (HCl 11%, 521 kg) and then with water (3×500 L) adjusting the pH to 7 with potassium carbonate in the last washing. The organic solution was concentrated by distillation under reduced pressure yielding 425 kg of ethyl 4-((2-ethoxy-2-oxoethyl)(methoxycarbonyl)amino)butanoate (assay 90.28% w/w). The product was purified by thin film distillation giving 410 kg of ethyl 4-((2-ethoxy-2-oxoethyl)(methoxycarbonyl)amino)butanoate having an assay of 96.59% w/w and purity of 98.77% A by GC (yield 76%).

Example 4

The procedure reported in example 3 was repeated affording 400 kg of ethyl 4-((2-ethoxy-2-oxoethyl)(methoxycarbonyl)amino)butanoate having an assay of 97.55% w/w and purity of 98.04% A by GC (yield 70%).

Example 5

Synthesis of dimethyl 5-hydroxy-3,6-dihydropyridine-1,4(2H)-dicarboxylate (Compound VI)

A reactor was charged with ethyl 4-((2-ethoxy-2-oxoethyl) (methoxycarbonyl)amino)butanoate (384 kg, assay 92.55% w/w) and methanol (3489 kg). The solution was heated up to T=40-45° C. and a solution prepared by mixing sodium methoxide 30% in methanol (27 kg) with methanol (152 kg) was added in 1 hour. The mixture was kept under stirring for eight hours at T=40-45° C. Glacial acetic acid (11 kg) was added and the resulting mixture was concentrated to residue by distillation. The residue was diluted with toluene (1670 kg). Further 410 kg of solvent were removed by distillation under reduced pressure. After the addition of sodium methoxide 30% in methanol (760 kg) the mixture was heated up to reflux for 5 hours. The mixture was concentrated by distillation removing 960 kg of solvent and then it was again diluted with toluene (768 kg) and the temperature was set to T=50-55° C. The toluene mixture was transferred into a second reactor charged with water (1920 kg), glacial acetic acid (384 kg) and sodium chloride (96 kg) while keeping the temperature between 10 and 20° C. The amount of toluene used in the washing (96 kg) was collected in the second reactor. The temperature was set at T=30-40° C. and the aqueous layer was separated. The organic layer was washed with a solution prepared by mixing water (960 kg) and sodium chloride (64 kg) and then with water (384 kg). The organic solution was concentrated by distillation at atmospheric pressure giving 622 kg of dimethyl 5-hydroxy-3,6-dihydropyridine-1,4(2H)-dicarboxylate in toluene (assay 38.31% w/w, yield 86%).

Example 6

The method described in Example 5 was repeated starting from 410 kg of ethyl 4-((2-ethoxy-2-oxoethyl)(methoxycarbonyl)amino)butanoate (assay 96.59% w/w) and obtaining 868 kg of dimethyl 5-hydroxy-3,6-dihydropyridine-1,4 (2H)-dicarboxylate in toluene (assay 26.26% w/w, yield 74%).

Example 7

Synthesis of dimethyl 1,4-dioxa-7-azaspiro[4.5] decane-7,10-dicarboxylate (Compound VII)

A solution of dimethyl 5-hydroxy-3,6-dihydropyridine-1, 4(2H)-dicarboxylate 32.2% w/w in toluene (434 kg) was charged into a reactor. The solution was made anhydrous by azeotropic distillation and then toluene was added to get in total 734 kg of solution. Ethylene glycol (86 kg) was added and the mixture was heated up to reflux and 50 kg of solvent were removed by distillation. To the solution was then added in 1.5 hours a mixture prepared by mixing anhydrous methanesulfonic acid (3.7 kg) and ethylene glycol (30 kg). The mixture was kept at reflux for 3 hours while distilling solvent and replacing it with the same amount of toluene. A further amount of anhydrous methanesulfonic acid (5 kg) and ethylene glycol (18 kg) was added in 35 minutes and the distillation was prosecuted for further 4 hours replacing the solvent removed by distillation with toluene. The mixture was then cooled down to T=30-40° C. and treated with potassium carbonate (4 kg), anhydrous disodium hydrogen phosphate (2 kg) and water (140 L) and the pH was adjusted to 7-8 units. The mixture was concentrated removing 435 kg of solvent by distillation at atmospheric pressure. The mixture was diluted with toluene (244 kg) and water (56 kg). Further 285 kg of solvent were removed by distillation at atmospheric pressure. The mixture was diluted with toluene (183 kg) and cooled down to T=50-60° C. The layers were separated. The aqueous layer was extracted with toluene (163 kg) at T=50-60° C. The organic layers were collected and concentrated by distillation at atmospheric pressure yielding 391 kg of dimethyl 1,4-dioxa-7-azaspiro[4.5]decane-7,10-dicarboxylate as toluenic solution.

Example 8

The preparation reported in example 7 was repeated affording 339 kg of dimethyl 1,4-dioxa-7-azaspiro[4.5]decane-7,10-dicarboxylate as toluenic solution.

Example 9

Synthesis of methyl 10-(hydroxycarbamoyl)-1,4-dioxa-7-azaspiro[4.5]decane-7-carboxylate (Compound VIII)

The solutions obtained in example 7 (391 kg) and 241 kg of that obtained in example 8 were combined. The mixture was concentrated to residue by distillation under reduced pressure. The residue was diluted with methanol (570 kg) and cooled to T=15-20° C. Hydroxylamine hydrochloride (120 kg) was charged into the reactor. Sodium methoxide 30% in methanol (624 kg) was added over 3.5 hours keeping the temperature in the range T=15-25° C. The mixture was further stirred at T=20° C. for 12 hours and then was cooled down to T=0-5° C. Hydrogen chloride (73 kg) was bubbled into the mixture till the pH was in the range 5-7 units. Acetone (100 kg) was charged and the mixture having a pH below 5 was kept under stirring for 2 hours at T=10-15° C. The pH was adjusted to 6-7 with sodium methoxide 30% in methanol (45 kg) and the suspension was cooled down to T=0-5° C. The salts were removed by filtration and were washed with methanol (160 kg). The filtrate was concentrated by distilling 780 kg of solvent under reduced pressure keeping the temperature below 40° C. The mixture was then diluted with n-butanol (54 kg) and concentrated further removing 530 kg of solvent by distillation. The residue was diluted at T=35-40° C. with a mixture of ethyl acetate (1056 kg) and methanol (12 kg). The mixture was concentrated by distilling 780 kg of solvent under reduced pressure. The residue was diluted with ethyl acetate (600 kg). Further 590 kg of solvent were removed by distillation under reduced pressure. The residue was diluted with ethyl acetate (750 kg) and kept at T=35-40° C. for 90 minutes. The suspension was cooled down to T=0-5° C. in 2.5 hours and kept at the same temperature for two hours. The product was isolated by filtration, washed with ethyl acetate and dried for 32 hours at T=35-40° C. under reduced pressure yielding 271.3 kg of methyl 10-(hydroxycarbamoyl)-1,4-dioxa-7-azaspiro[4.5]decane-7-carboxylate (assay 87.7% w/w, purity 98.8% A). Overall yield of 93% from dimethyl 5-hydroxy-3,6-dihydropyridine-1,4(2H)-dicarboxylate.

The invention claimed is:

1. A process for the manufacture of a compound of formula IX:

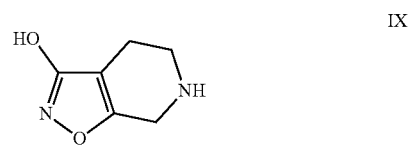

wherein the compound of formula IX is produced from a compound of formula VI:

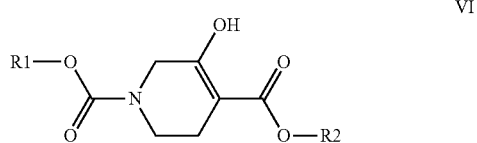

wherein R1 and R2 are methyl or ethyl; and wherein the compound of formula VI is manufactured by a process comprising the step:

(e) reacting a compound of formula V:

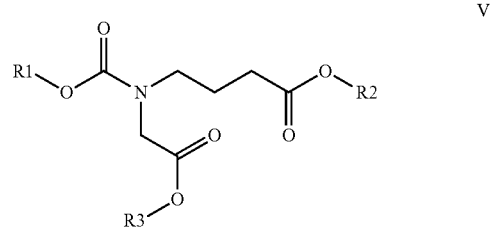

wherein R1, R2 and R3 are independently methyl or ethyl;

with sodium methoxide in methanol or sodium ethoxide in ethanol to obtain the compound of formula VI;

wherein R1 and R2 of the compound of formula VI are both methyl when sodium methoxide in methanol is used in the reaction, or R1 and R2 of the compound of formula VI are both ethyl when sodium ethoxide in ethanol is used in the reaction.

2. The process of claim 1, wherein the compound of formula V is manufactured by a process comprising the steps:
(b) reacting a compound of formula II:

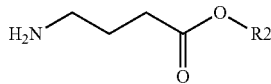

wherein R2 is methyl or ethyl;
with a base, and methyl glyoxylate or ethyl glyoxylate to obtain a compound of formula III:

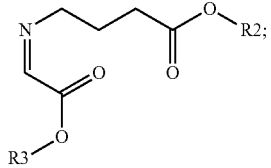

wherein:
R2 is methyl or ethyl; and
R3 is methyl when methyl glyoxylate is used in the reaction, or R3 is ethyl when ethyl glyoxylate is used in the reaction;
(c) converting the compound of formula III by hydrogenation to a compound of formula IV:

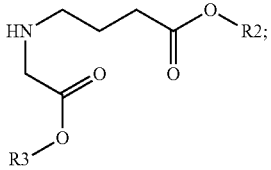

wherein R2 and R3 are independently methyl or ethyl; and
(d) reacting the compound of formula IV with methyl chloroformate or ethyl chloroformate to obtain the compound of formula V:

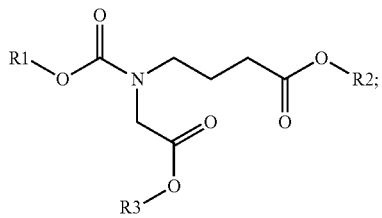

wherein:
R1 is methyl when methyl chloroformate is used in the reaction, or R1 is ethyl when ethyl chloroformate is used in the reaction; and
R2 and R3 are independently methyl or ethyl.
3. The process according to claim 2, wherein steps (b), (c) and (d) are carried out in toluene.

4. The process according to claim 2, wherein the base used in step (b) is triethylamine.
5. The process according to claim 2, wherein the compound of formula V is purified by thin-film distillation.
6. The process according to claim 2, wherein the compound of formula V is purified by washing with acidified water or by distillation or by a combination of these two purification strategies.
7. The process of claim 2, wherein the compound of formula II is produced by a process comprising the step:
(a) reacting a compound of formula I:

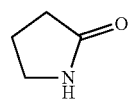

with an anhydrous acid, and methyl alcohol or ethyl alcohol.
8. The process according to claim 7, wherein the anhydrous acid is anhydrous methanesulfonic acid.
9. The process according to claim 8, wherein the compound of formula II is of formula IIb:

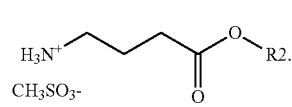

10. The process according to claim 9, wherein the compound of formula IIb is obtained by a one-pot synthesis.
11. The process according to claim 1, comprising reacting the compound of formula VI with ethylene glycol to obtain the compound of formula VII:

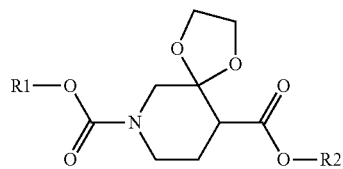

wherein R1 and R2 are methyl or ethyl.
12. The process according to claim 11, further comprising reacting the compound of formula VII with hydroxylamine to obtain the compound of formula VIII:

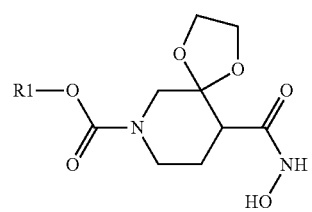

wherein R1 is methyl or ethyl.

13. The process according to claim 12, further comprising the step of converting the compound of formula VIII to the compound of formula IX.

\* \* \* \* \*